United States Patent
Martinez Vazquez et al.

(10) Patent No.: US 11,151,612 B2
(45) Date of Patent: Oct. 19, 2021

(54) AUTOMATED PRODUCT HEALTH RISK ASSESSMENT

(71) Applicant: International Business Machines Corporation, Armonk, NY (US)

(72) Inventors: Carlos Andres Martinez Vazquez, Tlaquepaque (MX); Emmanuel Barajas Gonzalez, Guadalajara (MX); Irving Yukio Hayashi Leon, Guadalajara (MX); Mara Miranda Bautista, Guadalajara (MX)

(73) Assignee: International Business Machines Corporation, Armonk, NY (US)

( * ) Notice: Subject to any disclaimer, the term of this patent is extended or adjusted under 35 U.S.C. 154(b) by 106 days.

(21) Appl. No.: 16/568,697

(22) Filed: Sep. 12, 2019

(65) Prior Publication Data

US 2021/0081998 A1 Mar. 18, 2021

(51) Int. Cl.
*G06Q 30/00* (2012.01)
*G06Q 30/02* (2012.01)
*G16H 50/30* (2018.01)
*G06Q 30/06* (2012.01)

(52) U.S. Cl.
CPC ..... *G06Q 30/0271* (2013.01); *G06Q 30/0267* (2013.01); *G06Q 30/0627* (2013.01); *G16H 50/30* (2018.01)

(58) Field of Classification Search
None
See application file for complete search history.

(56) References Cited

U.S. PATENT DOCUMENTS

| | | | |
|---|---|---|---|
| 2004/0006494 A1* | 1/2004 | Badinelli | G16H 70/40 705/2 |
| 2004/0117126 A1 | 6/2004 | Fetterman | |
| 2009/0309748 A1* | 12/2009 | Elgort | G06Q 30/02 340/686.6 |
| 2014/0156412 A1 | 6/2014 | Tse | |
| 2014/0188495 A1 | 7/2014 | Bi | |

(Continued)

OTHER PUBLICATIONS

STIC EIC 3600 Search Report for U.S. Appl. No. 16/568,697 dated Apr. 6, 2021. (Year: 2021).*

(Continued)

*Primary Examiner* — Matthew T Sittner
(74) *Attorney, Agent, or Firm* — Richard B. Thomas

(57) ABSTRACT

A computer-implemented method comprises analyzing an advertisement presented to a user during a first time period to identify a plurality of ingredients; and analyzing documents related to a medical condition of the user to determine a respective first relevance rank for each ingredient. The method further comprises selecting a subset of the ingredients having a highest number of occurrences based on the respective first relevance rank for each of the ingredients; performing sentiment analysis of the documents for the selected subset; determining a respective second relevance rank for each of the ingredients in the selected subset based on the sentiment analysis; and computing a product risk score based on the respective second relevance rank for each of the ingredients in the subset. The method further comprises modifying a display on a device associated with the user such that the display indicates the product risk score during the first time period.

16 Claims, 7 Drawing Sheets

(56) References Cited

U.S. PATENT DOCUMENTS

2014/0236622 A1    8/2014  Southam
2016/0112684 A1*   4/2016  Connor ................. A61B 5/1114
                                                                348/158
2017/0372197 A1*  12/2017  Baughman .............. A23L 33/30
2018/0144821 A1*   5/2018  Irani-Cohen ........... G16H 20/60

OTHER PUBLICATIONS

IP.com search strategy dated Apr. 7, 2021 (Year: 2021).*
Amran et al., "User Profile based Product Recommendation on Android Platform," 2014 5th International Conference on Intelligent and Advanced Systems (ICIAS), Jun. 3-5, 2014, 6 pages. <https://ieeexplore.ieee.org/document/6869557>.
Celik et al., "A Safety Food Consumption Mobile System through Semantic Web Technology," 2014 IEEE 38th Annual International Computers, Software and Applications Conference Workshops, Jul. 21-25, 2014, pp. 348-353. <https://ieeexplore.ieee.org/document/6903154>.
Mell et al., "The NIST Definition of Cloud Computing," Recommendations of the National Institute of Standards and Technology, U.S. Department of Commerce, Special Publication 800-145, Sep. 2011, 7 pgs.

* cited by examiner

AUTOMATED PRODUCT HEALTH RISK ASSESSMENT

BACKGROUND

It is common for advertising content to be presented in various forms of media, such as television, social networks, radio, etc. Depending on a user's medical history, some products can be harmful to the user that is viewing the advertisement. A user may not have easy access information regarding the product or potential affect of the product on the user's medical condition. Furthermore, even when such access is available, it is not conveniently accessed as it may require the user to interrupt other activities to determine any health risks of the product.

SUMMARY

Aspects of the disclosure may include a computer-implemented method, computer program product, and system for product risk assessment. One example of the computer-implemented method comprises analyzing an advertisement presented to a user during a first time period to identify a plurality of ingredients in a product in the advertisement; and analyzing one or more documents related to a medical condition of the user to determine a respective first relevance rank for each of the plurality of ingredients based, at least in part, on a number of occurrences of each ingredient in the one or more documents. The method further comprises selecting a subset of the plurality of ingredients having a highest number of occurrences based on the respective first relevance rank for each of the plurality of ingredients; performing sentiment analysis of the one or more documents for the selected subset of the plurality of ingredients having the highest number of occurrences; determining a respective second relevance rank for each of the ingredients in the selected subset of the plurality of ingredients based on the sentiment analysis; and computing a product risk score for the product based on the respective second relevance rank for each of the ingredients in the subset of the plurality of ingredients. The product risk score indicates a risk for effects of the product on the medical condition of the user. The method further comprises modifying a display on a device associated with the user such that the display indicates the product risk score for the product during the first time period in which the advertisement is presented to the user.

DRAWINGS

Understanding that the drawings depict only exemplary embodiments and are not therefore to be considered limiting in scope, the exemplary embodiments will be described with additional specificity and detail through the use of the accompanying drawings, in which.

Figure 5:
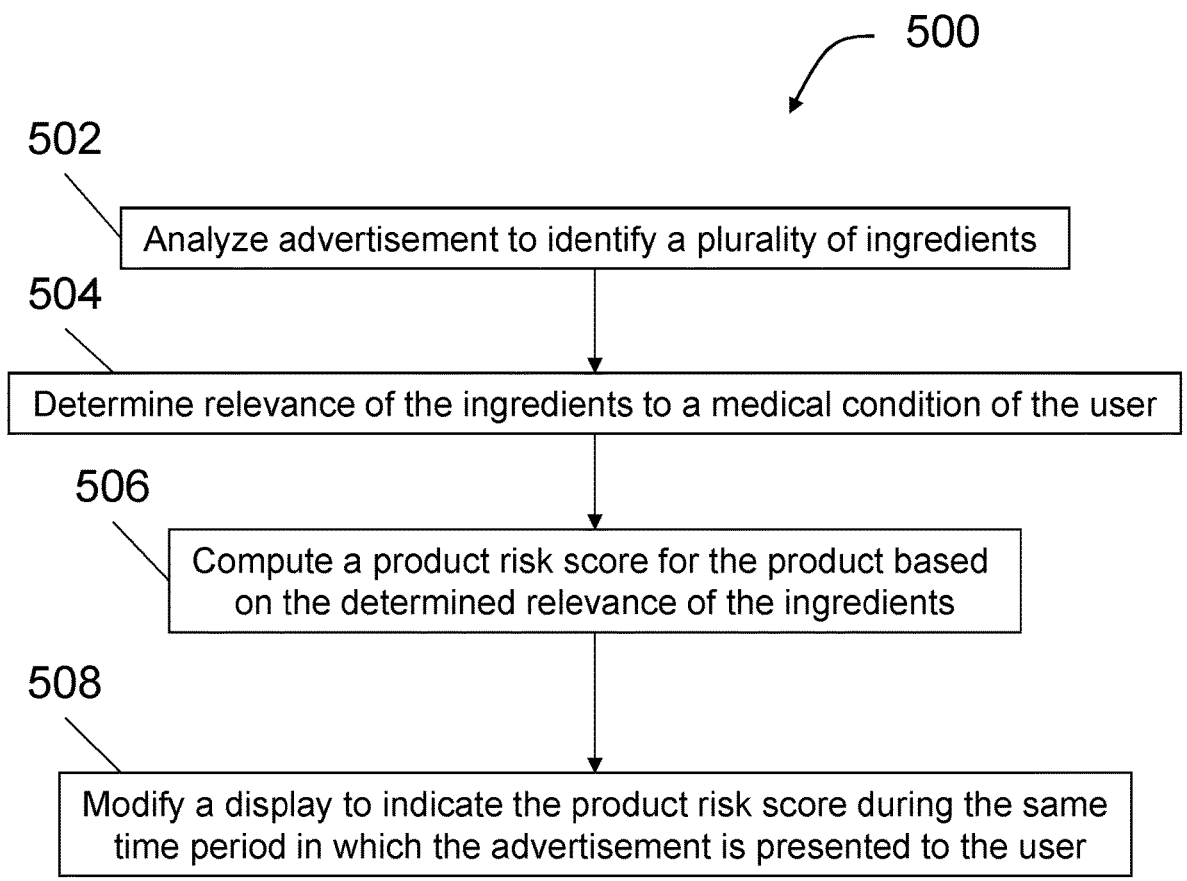

FIG. 5 a flow chart depicting one embodiment of an example method for product risk assessment.

Figure 6:
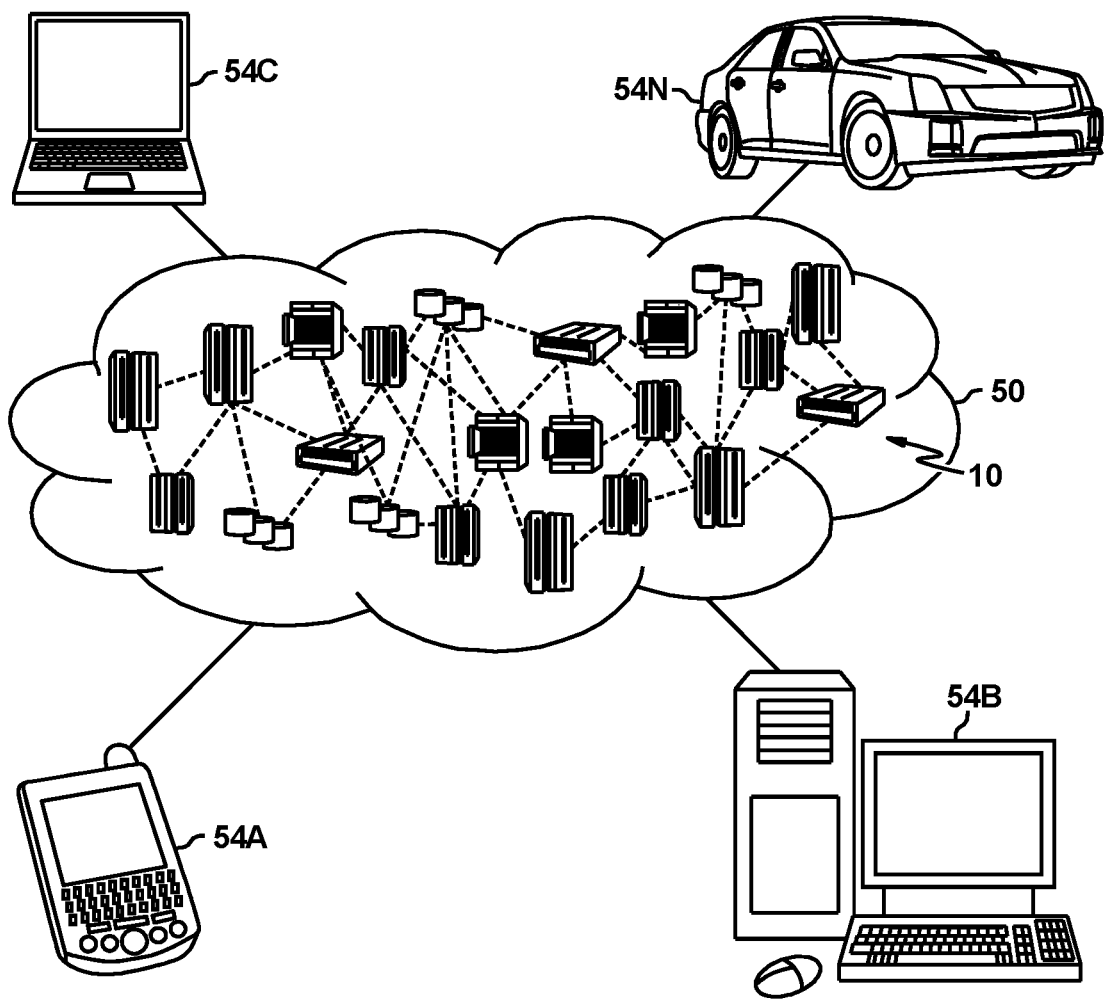

FIG. 6 depicts a cloud computing environment according to an embodiment of the present disclosure.

Figure 7:
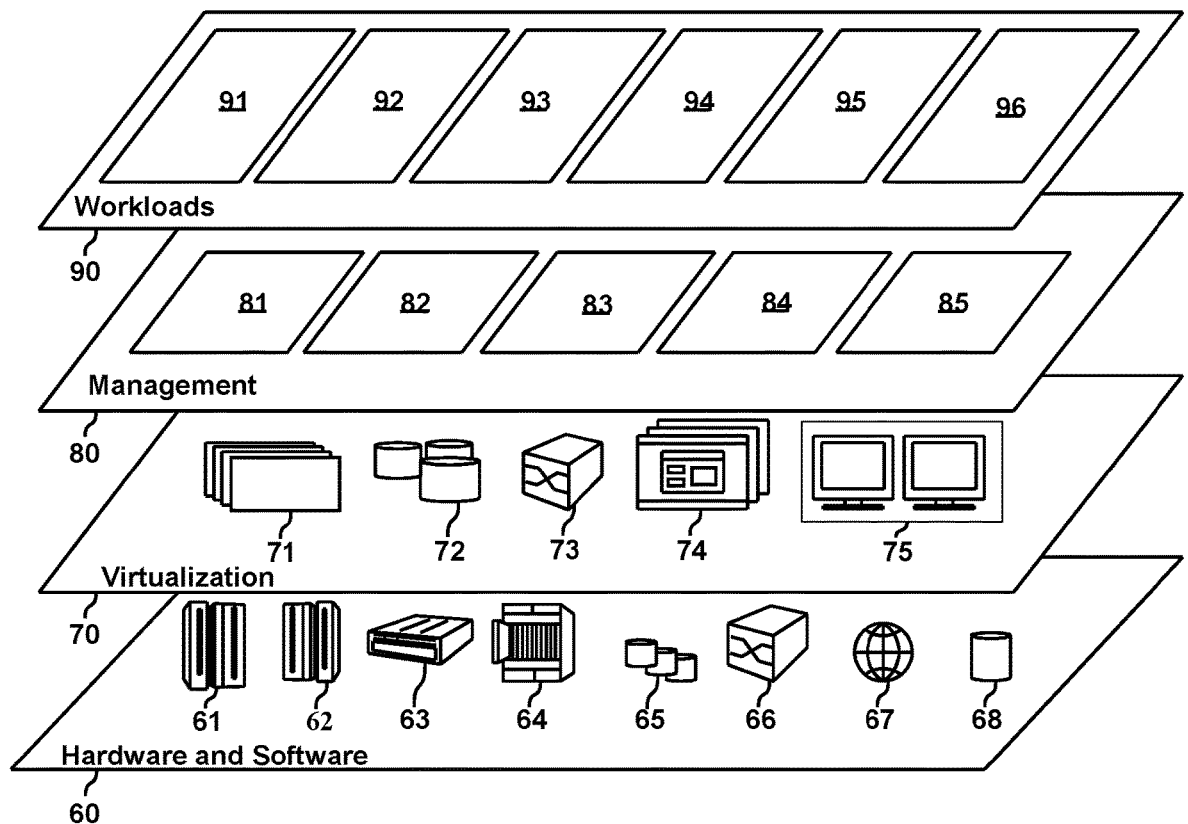

FIG. 7 depicts abstraction model layers according to an embodiment of the present disclosure.

In accordance with common practice, the various described features are not drawn to scale but are drawn to emphasize specific features relevant to the exemplary embodiments.

DETAILED DESCRIPTION

In the following detailed description, reference is made to the accompanying drawings that form a part hereof, and in which is shown by way of illustration specific illustrative embodiments. However, it is to be understood that other embodiments may be utilized and that logical, mechanical, and electrical changes may be made. Furthermore, the method presented in the drawing figures and the specification is not to be construed as limiting the order in which the individual steps may be performed. The following detailed description is, therefore, not to be taken in a limiting sense.

Figure 1:
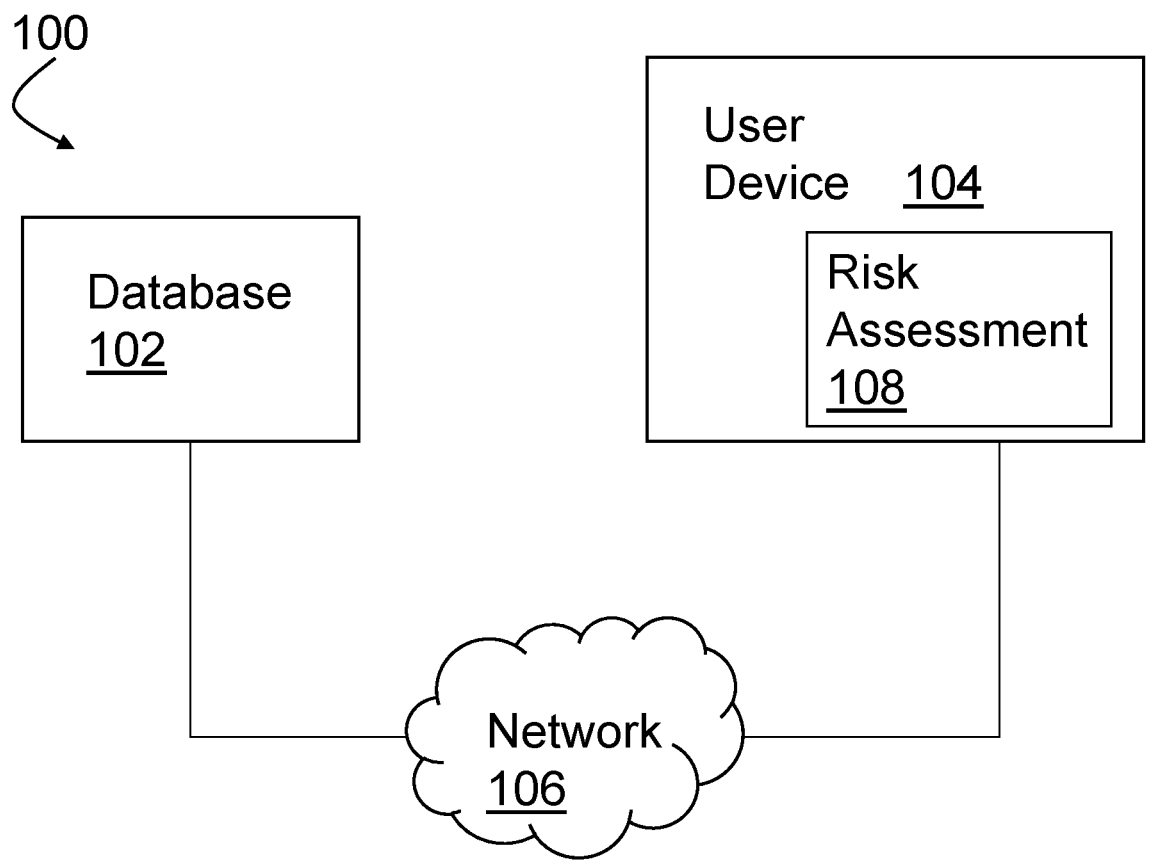
FIG. 1 is a high-level block diagram depicting one embodiment of an example product health risk assessment system.

FIG. 1 is a high-level block diagram depicting one embodiment of an example product health risk assessment system 100. System 100 includes a database 102 connected to at least one user device 104 via a network 106. The network 106 can be implemented using any number of any suitable physical and/or logical communications topologies. The network 106 may include one or more private or public computing networks. For example, network 106 may comprise a private network (e.g., a network with a firewall that blocks non-authorized external access) that is associated with the workload. Alternatively, or additionally, network 106 may comprise a public network, such as the Internet. Thus, network 106 may form part of a packet-based network, such as a local area network, a wide-area network, and/or a global network such as the Internet. Network 106 can include one or more servers, networks, or databases, and can use one or more communication protocols to transfer data between the database 102 and user device 104. Additionally, the network 106 can transfer data from a content provider (not shown) to the user device 104.

Furthermore, although illustrated in FIG. 1 as a single entity, in other examples network 106 may comprise a plurality of networks, such as a combination of public and/or private networks. The communications network 106 can include a variety of types of physical communication channels or "links." The links can be wired, wireless, optical, or any other suitable media. In addition, the communications network 106 can include a variety of network hardware and software for performing routing, switching, and other functions, such as routers, switches, base stations, bridges or any other equipment that may be useful to facilitate communicating data.

The user device 104 can include one or more mobile devices of the user (such as, but not limited to, a smart phone, tablet, activity tracker, wearable device, augmented reality (AR)/virtual reality (VR) device, etc.) and/or other devices of the user (such as, but not limited to, a desktop computer, laptop computer, or smart television, etc.). The user device 104 in the example shown in FIG. 1 is configured to implement risk assessment functionality 108 such that the user device 104 performs health risk analysis on products contained in advertisements (also referred to herein as "ads") provided to the user device 104, as described herein. For example, the advertisements can be in the form of videos (such as, but not limited to, television video ads), static images (such as, but not limited to, banner ads on a webpage), and audio (such as, but not limited to, radio ads), and/or a combination thereof. The advertisements can be provided to the user device 104 via the network 106, in some embodiments. In other embodiments, the advertisements can be provided via other communication channels. For example, a radio ad or television ad can be communicated to the user device 104 via over-the-air broadcast radio frequency transmissions rather than over the network 106, in some embodiments.

The user device 104 is configured to analyze the received ad to identify a product being advertised. For example, the user device 104 can be configured to use various image analysis techniques, natural language processing techniques, and cognitive analysis techniques in performing the functionality described herein. Such techniques can include, but are not limited to, optical character recognition (OCR), edge detection, neural networks (e.g. Convolutional Neural Networks or Recurrent Neural Networks), syntactic analysis, semantic analysis, sentiment analysis, word ranking techniques (e.g. term frequency-inverse document frequency (TF-IDF)), regression algorithms (e.g. linear regression or logistic regression), instance-based algorithms (e.g. k-nearest neighbor or Support Vector Machines), decision tree algorithms, Bayesian algorithms, clustering algorithms (e.g. k-means or hierarchical clustering), etc.

When the product is identified as a product which can be consumed (e.g. food or medicine) by the user of user device 104, the risk assessment functionality 108 of user device 104 is configured to determine a risk of the product to the health of the user. In particular, the user device 104 accesses a medical profile of the user stored in database 102. It is to be understood that access to the medical profile of the user can be conditioned on authorization for such access given by the user enabling the user to opt-in to such uses of the user's medical information or profile. The medical profile can include information such as allergies, disorders, or other diagnosed medical conditions/diseases, etc. The user device 104 can use analysis techniques, such as the example techniques discussed above to identify such information in the medical profile. Furthermore, in other embodiments, the user can input an explicit medical condition through a user interface of user device 104 in lieu of or in addition to granting access to the user's medical profile.

In addition to identifying a product consumable by the user in a received ad, the user device 104 is also configured to identify ingredients of the product in the received ad. For example, visual recognition/image analysis techniques, such as those discussed above, can be used to identify a barcode of the product which can be used to identify the product and its ingredients from a database, such as database 102, accessed over the network 106, in some embodiments. In other embodiments, image analysis and/or natural language processing techniques, such as those discussed above, can be used to extract audio and/or image data from the advertisement to identify the product and information regarding the ingredients can be obtained from a database accessed over the network 106. In yet other embodiments, image analysis and natural language processing techniques can be used to analyze an image of the product's label which lists ingredients. Thus, the ingredients, in such embodiments, can be obtained without accessing a separate database over the network 106.

Additionally, the user device 104 can access medical condition information from database 102. Although, for convenience of explanation in describing the example of FIG. 1, the medical profile and medical condition information are contained in the same database 102 in this example, it is to be understood that the medical profile and the medical condition information can be stored on different databases in other embodiments. Furthermore, it is to be understood that the medical condition information can be contained on multiple different databases. For example, the medical condition information can include data from public databases, such as those maintained by government entities, databases containing medical papers or research, private or proprietary medical information databases, etc. The medical condition information can include recently published information as well as information on topics widely studied. The user device 104 is configured to correlate a medical condition of the user from the medical profile with information regarding the specific medical condition of the user from the medical condition databases. This correlation can be done using image analysis techniques, natural language processing techniques, and cognitive analysis techniques such as those mentioned above. In some embodiments, this correlation is done prior to receiving and/or analyzing advertisements on user device 104. This correlation includes identifying/selecting documents and/or parts of documents from the medical condition databases that are related to the specific medical condition of the user.

The user device 104 correlates the medical profile of the user with information regarding the diagnosed condition to determine relevance and impact of particular foods and ingredients of the advertised product to the diagnosed condition of the user. For example, in some embodiments, the user device 104 can perform TF-IDF analysis on the correlated medical condition information to determine which of the product ingredients are relevant to the user's medical condition. That is, at a high level, the user device 104 identifies ingredients that appear most frequently in documents discussing the user's identified medical condition. The TF-IDF analysis takes into consideration both the frequency of use of the ingredient within a given a document as well as the number of documents which contain or make reference to the ingredient. In some such embodiments, the user device 104 ranks the ingredients based on the determined relevance and selects a subset of those ingredients based on the ranking (e.g. the five most frequently used or most relevant ingredients based on the ranking).

In some such embodiments, the user device 104 performs sentiment analysis on the selected subset of ingredients to determine treatment of the ingredients in the subset. For example, a given ingredient, such as sugar, may be frequently used in documents discussing a medical condition. However, sentiment analysis may determine that words around the term 'sugar' indicate that sugar has little to no effect on the user's medical condition. In contrast, another ingredient may not be mentioned as frequently as sugar, but the sentiment analysis may indicate that it has a greater effect on the medical condition. Thus, the user device 104 re-ranks the relevance of the ingredients in the selected subset based on the sentiment analysis, in some such embodiments. Thus, a first ingredient in the subset which is used less frequently than a second term in the subset can be ranked higher than the second term after performing the sentiment analysis. In some embodiments, the ranking is a numerical ranking. However, other techniques for ranking can be used in other embodiments. For example, the terms can be ranked or categorized into a pre-defined set of categories, such as low, medium, and high relevance to the given medical condition.

Based on the correlation and ranking of the ingredients, the user device 104 computes a score for the product indicating the product's effect on the user's medical condition. For example, in some embodiments, a score is computed for each ingredient in the product's list of ingredients. In other embodiments, a single score is computed for the product as a whole based on the relative importance of each of the ingredients to the user's medical condition. Furthermore, in some embodiments, the score is a numerical value. In other embodiments, the product score categorizes the product into a predetermined set of categories, such as, Beneficial, Benign, or Harmful. In yet other embodiments, a score is only computed for products determined to have a negative or harmful effect on the user's medical condition.

Additionally, in some embodiments, the user device 104 is configured to obtain quantities of each identified ingredient in the product. For example, the quantities of each ingredient can be listed in the database containing the ingredient information for the product, in some embodiments. In other embodiments, a relative estimate of the quantity of each ingredient can be determined by the user device 104 based on the order of the ingredients on the product label. In embodiments in which the quantity of each ingredient is determined or estimated, the user device 104 includes the quantity of the ingredients in the score computed for the product. For example, although an ingredient is identified as harmful for the user's medical condition, it may only be harmful if sufficient quantities are consumed. In such an example, if the quantify of the ingredient is sufficiently low in the product, the score may indicate a low risk or no risk, etc. based on the ingredient's quantity and effect. Similarly, the medical condition information may indicate that an ingredient normally has little effect unless more than a given quantity is consumed. If it is determined that the product contains more than that given quantity of the ingredient, the score can be adjusted to indicate an increased risk based on the quantity (e.g. changing from benign to harmful based on quantity).

The user device 104 is configured to modify a display based on the computed score for the advertised product. For example, in some embodiments, the user device 104 is configured to overlay a notice on top of the displayed advertisement. In some such embodiments, the overlaid notice can be a banner over a portion of the displayed static image or video stream. Alternatively, the notice can be overlaid in a specified location of the display regardless of which portion of the screen contains the advertisement, in other embodiments. In some such embodiments, the user can specify the location for the notice. The notice can be configured, in some embodiments, to display information such as the name of the product, the product score, ingredient list, individual ingredient scores, the medical condition effected and/or the effect of the ingredient(s) on the medical condition. The information to be displayed can be configured by the user in some embodiments. Furthermore, in some embodiments, the user device 104 is configured to simply display a color indicating a risk of the product to the user's health. For example, the user device 104 can cause the display to display a color such as red for harmful, yellow for benign, and green for beneficial, in some embodiments. The color can be displayed as a border around the screen or as a colored box overlaying a portion of the screen. As noted above, in some embodiments, the user device 104 only causes the display to be modified if one or more ingredients of the product are determined to have a possible negative effect on the health of the user based on the user's medical profile and diagnosed medical conditions.

Furthermore, in some embodiments, modification of the display can include modifications to the display of the advertisement. For example, in some embodiments, the user device 104 can be configured to stop streaming a video advertisement, mute audio of an advertisement, place an obscuring filter over the advertisement to obscure viewing the advertisement, replace a static image of the advertisement with a different image or text, change a channel of a television, etc. The manner in which the display is modified can be determined according to user preferences in some embodiments. Thus, through the above cognitive analysis of received advertisements, user medical profile, and medical condition information, the embodiments described herein provide numerous advantages and benefits. In addition to informing the user of possible health effects of products, which may not have been known to the user or not readily available, the embodiments herein improve the display by enabling the display and communication of relevant health information in association with the concurrently displayed advertisement. This modification of the display improves the ease of access to the information for the user as well as context for the information by enabling the dynamic and automated analysis of the advertisement to then provide the information substantially concurrently with the display of the advertisement.

Figure 2:
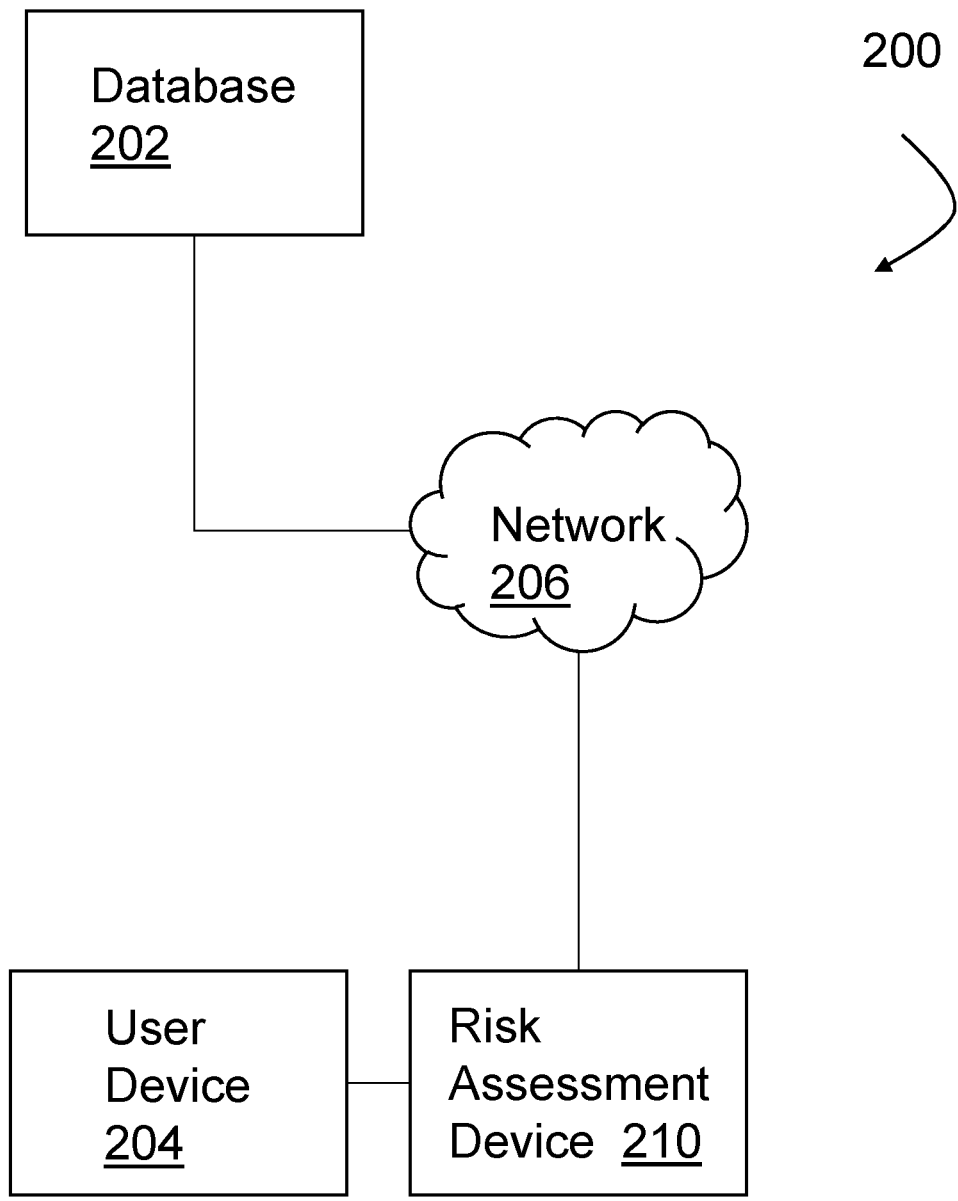
FIG. 2 is a high-level block diagram depicting another embodiment of an example product health risk assessment system.

Furthermore, it is to be understood that although the user device 104 is described in FIG. 1 as performing the analysis of the advertisements and ingredients in the advertised products, it is to be understood that the above functionality can be distributed among other devices in addition to or in lieu of the user device 104. For example, FIG. 2 is a high-level block diagram depicting another embodiment of an example product health risk assessment system 200. In FIG. 2, system 200 includes database 202 and network 206 similar to database 102 and network 106 in FIG. 1. For example, database 202 can be implemented as one or more databases containing medical profiles, medical condition information, product information, etc., as discussed above. Additionally, network 206 can be implemented using any number of any suitable physical and/or logical communications topologies, similar to network 106. However, in FIG. 2, user device 204 does not include the same risk assessment functionality 108 which user device 104 includes. Rather, all or part of the risk assessment functionality 108 is implemented in risk assessment device 210.

For example, in some embodiments, risk assessment device 210 performs the functionality of analyzing received ads to determine the ingredients (and quantities of ingredients) of products in the received ads, correlating the ingredients to the user's medical profile, determining relevance of ingredients to a medical condition based on analysis of data in one or more medical condition databases, etc. The risk assessment device 210 then outputs to the user device 204 commands to modify the display of the user device 204 based on the calculated risk assessment, as discussed above.

In other embodiments, the risk assessment device 210 performs part of the functionality discussed above with respect to risk assessment functionality 108 and user device 104. For example, in some such embodiments, the risk assessment device 210 analyzes the user's medical profile and the medical condition information to identify documents which relate to the user's medical condition. The risk assessment device 210 in such embodiments can also analyze ads prior to the ad being delivered to the user device. Thus, in some embodiments, the ads are routed to the risk assessment device 210 prior to being forwarded from the risk assessment device 210 to the user device 204. In some such embodiments, the risk assessment device 210 identifies the product in the ad and extracts the product's ingredients and quantities. The risk assessment device 210 then forwards the extracted ingredients, the ad, and the results of the correlation between the medical profile and the medical condition information to the user device 204. The user device 204 uses the received information to determine the risk or possible effects of the ingredients on the user's medical condition and modifies the display on the user device 204 accordingly. Thus, in such embodiments, part of the risk assessment functionality is performed on the risk assessment device 210 and part is performed by the user device 204.

Figure 3:
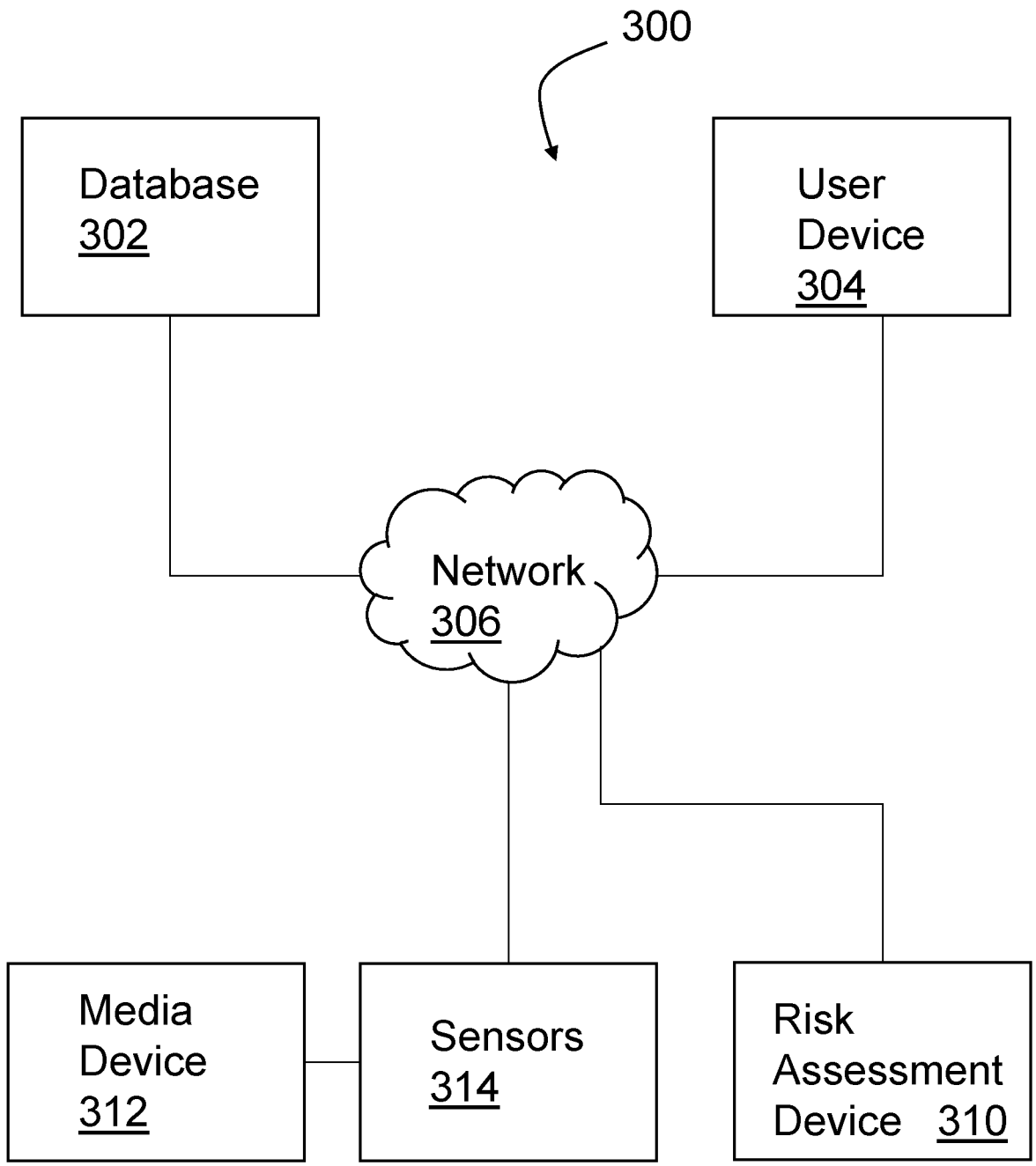
FIG. 3 is a high-level block diagram depicting another embodiment of an example product health risk assessment system.

FIG. 3 is a high-level block diagram of another embodiment of an example product health risk assessment system 300. Similar to example systems 100 and 200, system 300 includes a database 302 and a network 306. As discussed above, a single database 302 is depicted for ease of explanation, but it is to be understood that more than one database can be used in other embodiments. For example, as discussed above one or more databases can be used to store medical profiles of users, one or more databases can be used to store medical condition information, and one or more databases can be used to store product information. The network 306 is similar to network 106 and 206 above.

System 300 includes a user device 304 and a media device 312. In this example, the advertisement is displayed or otherwise output on media device 312 rather than user device 304. For example, the media device 312 can be a television, radio, etc. In the example of FIG. 3, the system 300 includes one or more sensors 314 located in the environment around the media device 312. The sensors are configured to obtain information regarding the advertisement being output on the media device 312. For example, the sensors 314 can include one or more cameras and/or one or more microphones, etc. Thus, the sensors 314 can collect image data and/or audio data pertaining to the advertisement output on the media device 312. The sensors provide the obtained advertisement data to the risk assessment device 310 in this example. In particular, in this example, the risk assessment device 310 is coupled to the sensors 314 via network 306. However, in other embodiments, the risk assessment device 310 can be directly coupled to the sensors 314 via a local network or direct connection rather than over a wide area network such as the internet.

The risk assessment device 310 is configured to perform the analysis of the advertisement data as well as medical profile data and medical condition information from database 302, as described above with respect to FIGS. 1 and 2. As discussed above with respect to risk assessment device 210, the risk assessment device 310 can perform all or part of the risk assessment functionality discussed above with respect to user device 104. In some embodiments, the risk assessment device 310 calculates a risk assessment score for one or more ingredients or for the product as a whole and outputs commands to user device 304 to modify a display of user device 304 accordingly. In other embodiments, the risk assessment device 310 outputs extracted product information from the advertisement data as well as correlations based on the medical profile and medical condition information to the user device 304 and the user device 304 performs the final analysis to determine the risk or score for the product and adjust the display of the user device 304 accordingly.

In some embodiments, the user device 304 is configured to notify the user regarding the score for the product in the advertisement being output on the media device 312. For example, the user device 304 can be configured to flash a color, to vibrate, and/or to output a sound or other audio message related to the advertisement being output on the media device 312. For example, the user device 304 can output an audio message indicating that the displayed product includes a certain ingredient which may negatively impact a medical condition of the user. Thus, in some such embodiments, the user device 304 can be a speaker coupled to the risk assessment device 310. In other such embodiments, the user device 304 is a computing device of the user such as a smartphone, tablet, fitness tracker, VR device or other wearable smart device, etc. In other embodiments, the user device 304 is configured to output a display on a screen of the user device 304, as discussed above. In other embodiments, the user device 304 is configured to output a notification similar to a notification for a received email or text message on a smart phone or wearable device. The user device 304 is configured to notify the user substantially concurrently with the output of the advertisement on the media device 312. Thus, such embodiments enable the advantages discussed above even with the use of media devices, such as but not limited to non-smart televisions or radios, that are not connected to a network 306 or otherwise not configured to display such notifications regarding the health assessment.

In the example shown in FIG. 3, the system 300 includes a risk assessment device 310. However, it is to be understood that in other embodiments, the risk assessment device 310 can be omitted. For example, the user device 304, in some such embodiments, can be configured to include risk assessment functionality such as risk assessment functionality 108 in user device 104 of FIG. 1. Thus, it is to be understood that modifications to the components of system 300, system 200, and system 100 can be made in other embodiments.

Figure 4:
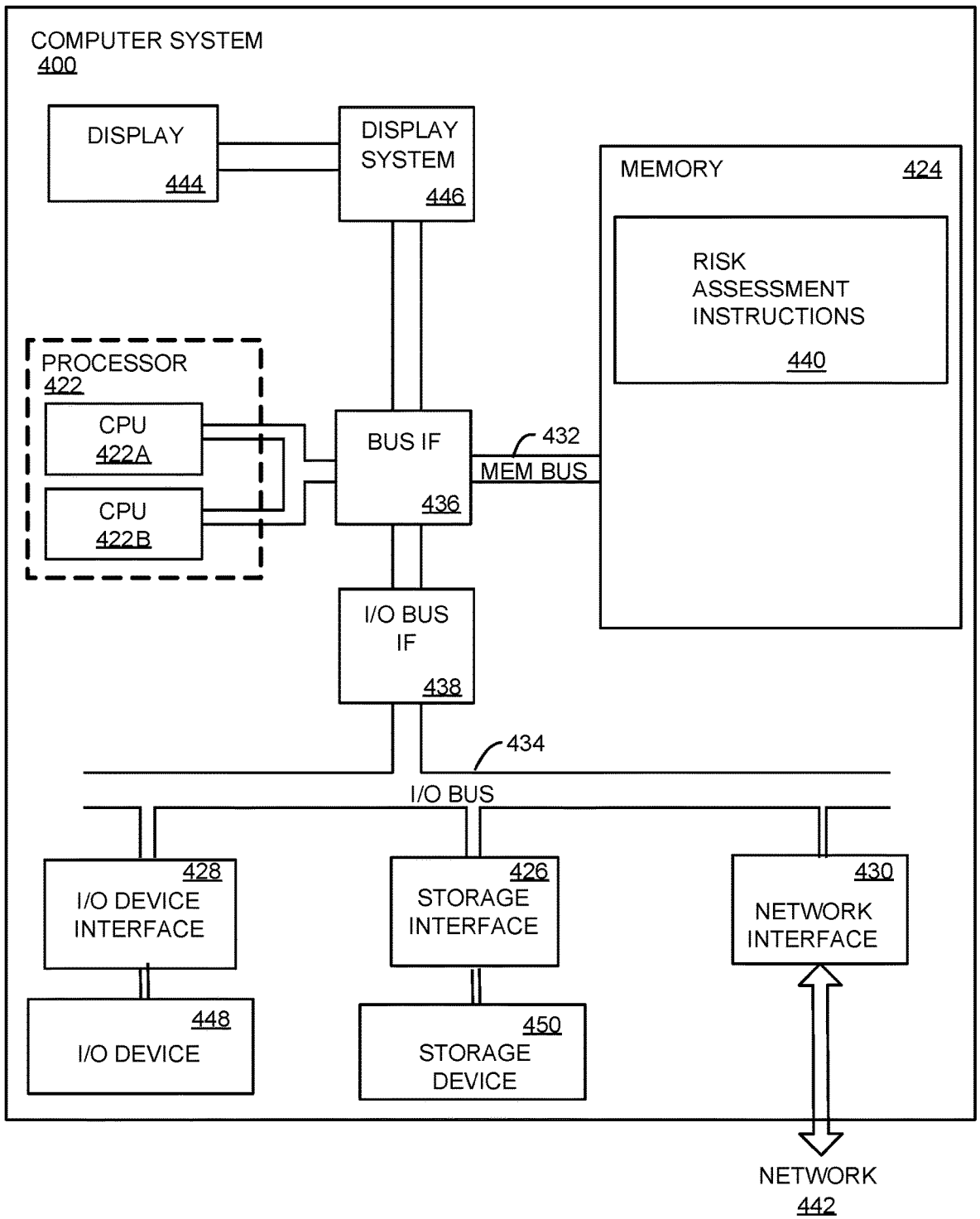
FIG. 4 is a high-level block diagram of one embodiment of an example computer system.

FIG. 4 is a high-level block diagram of one embodiment of an example computer system 400 configured to implement the functions discussed above. In particular, the computer system 400 can be implemented as a user device such as user device 104, 204, or 304. The components of the computer system 400 shown in FIG. 4 include one or more processors 422, a memory 424, a storage interface 426, an Input/Output ("I/O") device interface 428, and a network interface 430, all of which are communicatively coupled, directly or indirectly, for inter-component communication via a memory bus 432, an I/O bus 434, bus interface unit ("IF") 436, and an I/O bus interface unit 438.

In the embodiment shown in FIG. 4, the computer system 400 also includes one or more general-purpose programmable central processing units (CPUs) 422A and 422B, herein generically referred to as the processor 422. In some embodiments, the computer system 400 contains multiple processors. However, in other embodiments, the computer system 400 is a single CPU system. Each processor 422 executes instructions stored in the memory 424.

In some embodiments, the memory 424 includes a random-access semiconductor memory, storage device, or storage medium (either volatile or non-volatile) for storing or encoding data and programs. For example, the memory 424 may store risk assessment instructions 440. In some embodiments, the memory 424 represents the entire virtual memory of the computer system 400 and may also include the virtual memory of other computer systems coupled directly to the computer system 400 or connected via a network 442. In some embodiments, the memory 424 is a single monolithic entity, but in other embodiments, the memory 424 includes a hierarchy of caches and other memory devices. For example, the memory 424 can exist in multiple levels of caches, and these caches may be further divided by function, so that one cache holds instructions while another holds non-instruction data, which is used by the processor. The memory 424 may be further distributed and associated with different CPUs or sets of CPUs, as is known in any various so-called non-uniform memory access (NUMA) computer architectures, for example.

Hence, although the risk assessment instructions 440 is stored on the memory 424 in the example shown in FIG. 4 for purposes of explanation, it is to be understood that other embodiments can be implemented differently. For example, the risk assessment instructions 440 can be distributed across multiple physical media in some embodiments.

Furthermore, in some embodiments, the risk assessment instructions 440 are executed by the same processor 422. However, in other embodiments, execution of the risk assessment instructions 440 is distributed across multiple processors located in the same or different computer systems. For example, in some such embodiments, at least a portion of the instructions and data structures associated with the risk assessment instructions 440 can be on different computer systems and accessed remotely, e.g., via a network 442. The computer system 400 can use virtual addressing mechanisms that allow the programs of the computer system 400 to behave as if they only have access to a large, single storage entity instead of access to multiple, smaller storage entities. Thus, the memory 424 can store all or a portion of the various programs, modules, and data structures for performing the risk assessment functionality, as discussed herein.

The computer system 400 in the embodiment shown in FIG. 4 also includes a bus interface unit 436 to handle communications among the processor 422, the memory 424, the display system 444, and the I/O bus interface unit 438. The I/O bus interface unit 438 is coupled with the I/O bus 434 for transferring data to and from the various I/O units. In particular, the I/O bus interface unit 438 can communicate with multiple I/O interface units 428, 426, and 430, which are also known as I/O processors (IOPs) or I/O adapters (IOAs), through the I/O bus 434. The display system 446 includes a display controller, a display memory, or both. The display controller can provide video, audio, or both types of data to a display device 444. The display memory may be a dedicated memory for buffering video data. The display system 446 is coupled with the display device 444, such as a standalone display screen, computer monitor, television, a tablet or handheld device display, or another displayable device. In some embodiments, the display device 444 also includes one or more speakers for rendering audio. Alternatively, one or more speakers for rendering audio may be coupled with an I/O interface unit. In alternate embodiments, one or more functions provided by the display system 446 are on board an integrated circuit that also includes the processor 422. In addition, in some embodiments, one or more of the functions provided by the bus interface unit 436 is on board an integrated circuit that also includes the processor 422.

The I/O interface units support communication with a variety of storage and I/O devices. For example, the I/O device interface unit 428 supports the attachment of one or more user I/O devices 448, which may include user output devices (such as a video display devices, speaker, fax machine, printer, and/or television set) and user input devices (such as a keyboard, mouse, keypad, touchpad, trackball, buttons, light pen, or other pointing devices). A user can manipulate the user input devices 448 using a user interface, in order to provide input data and commands to the user I/O device 448 and the computer system 400. Additionally, a user can receive output data via the user output devices. For example, a user interface may be presented via the user I/O device 448, such as displayed on a display device, played via a speaker, or printed via a printer.

The storage interface 426 supports the attachment of one or more disk drives or direct access storage devices 450 (which are typically rotating magnetic disk drive storage devices, although they could alternatively be other storage devices, including arrays of disk drives configured to appear as a single large storage device to a host computer, or solid-state drives, such as a flash memory). In another embodiment, the storage device 450 is implemented via any type of secondary storage device. The contents of the memory 424, or any portion thereof, may be stored to and retrieved from the storage device 450 as needed. The network interface 430 provides one or more communication paths from the computer system 400 to other digital devices and computer systems.

In operation, the processor 422 is configured to execute risk assessment instructions 440 to implement the functionality described above. For example, risk assessment instructions 440 are configured, in some embodiments, to cause the processor 422 to preform the functions of extracting product information from an advertisement, correlating a user's medical profile with information regarding a diagnosed medical condition from a medical condition database, calculate a risk score for the advertised product, and/or output commands to modify a display on the display 444 to provide notification/information to the user regarding the health risk associated with that product and the user's medical profile. Additional details regarding an example method of providing the risk assessment which can be performed by processor 422 are described below with respect to FIG. 5.

Although the computer system 400 shown in FIG. 4 illustrates a particular bus structure providing a direct communication path among the processors 422, the memory 424, the bus interface 436, the display system 446, and the I/O bus interface unit 438, in alternative embodiments the computer system 400 includes different buses or communication paths, which may be arranged in any of various forms, such as point-to-point links in hierarchical, star or web configurations, multiple hierarchical buses, parallel and redundant paths, or any other appropriate type of configuration. Furthermore, while the I/O bus interface unit 438 and the I/O bus 434 are shown as single respective units, the computer system 400, can include multiple I/O bus interface units 438 and/or multiple I/O buses 434 in other embodiments. While multiple I/O interface units are shown, which separate the I/O bus 434 from various communication paths running to the various I/O devices, in other embodiments, some or all of the I/O devices are connected directly to one or more system I/O buses.

Furthermore, it is to be understood that the components shown in FIG. 4 are provided by way of example only and that, in other embodiments, other components in addition to or in lieu of those shown can be used and that some components shown in FIG. 4 can be omitted. For example, although the computer system 400 is shown and described as being implemented as a user device, such as user device 104, in this example, the computer system 400 can be implemented as a risk assessment device such as risk assessment device 210 or 310 in other embodiments. In some such embodiments, the computer system 400 is a multi-user mainframe computer system, a single-user system, or a server computer or similar device that has little or no direct user interface, but receives requests from other computer systems (clients). In such embodiments, the display 444 and display system 446 can be omitted. In other embodiments, the computer system 400 is implemented as a user device having a user interface, such as a desktop computer, portable computer, laptop or notebook computer, tablet computer, pocket computer, telephone, smart phone, or any other suitable type of electronic device. In some such embodiments, the storage interface 426 and storage device 450 can be omitted, for example.

In addition, in some embodiments, the computer system 400 can be implemented within a cloud computer system, or using one or more cloud computing services. Consistent with various embodiments, a cloud computer system can include a network-based, distributed data processing system that provides one or more cloud computing services. In certain embodiments, a cloud computer system can include many computers, hundreds or thousands of them, disposed within one or more data centers and configured to share resources over the network. However, it is to be understood that cloud computer systems are not limited to those which include hundreds or thousands of computers and can include few than hundreds of computers. Some example cloud computing embodiments are discussed in more detail below.

As discussed above, in some embodiments, one or more of the components and data shown in FIG. 4 include instructions or statements that execute on the processor 422 or instructions or statements that are interpreted by instructions or statements that execute the processor 422 to carry out the functions as described herein. In other embodiments, one or more of the components shown in FIG. 4 are implemented in hardware via semiconductor devices, chips, logical gates, circuits, circuit cards, and/or other physical hardware devices in lieu of, or in addition to, a processor-based system.

FIG. 5 is a flow chart depicting one embodiment of an example method 500 for product risk assessment. Method 500 can be implemented by a node, such as user device 104, 204, 304 or risk assessment device 210 or 310. For example, the method 500 can be implemented by a CPU, such as CPU 422 in computer system 400, executing instructions, such as risk assessment instructions 440. It is to be understood that the order of actions in example method 500 is provided for purposes of explanation and that the method can be performed in a different order in other embodiments. Similarly, it is to be understood that some actions can be omitted or additional actions can be included in other embodiments.

At 502, an advertisement presented to a user during a first time period is analyzed to identify a plurality of ingredients in a product in the advertisement. For example, as discussed above, analyzing the advertisement can include, in some embodiments, performing image analysis on the advertisement to identify a barcode of the product, identifying the product in a product database based on the barcode, and obtaining the plurality of ingredients from the product database. Furthermore, in some embodiments, analyzing the advertisement can include determining a quantity of each of the plurality of ingredients in the product. For example, in some embodiments, the quantity of each ingredient can be obtained from a product database. In other embodiments, the quantity of each ingredient can be estimated based on an order of listed ingredients on a label, as discussed above.

At block 504, relevance of the plurality of ingredients to the medical condition of the user is determined, as discussed above. For example, in some embodiments, determining the relevance of the plurality of ingredients includes analyzing one or more documents related to a medical condition of the user to determine a respective first relevance rank for each of the plurality of ingredients based, at least in part, on a number of occurrences of each ingredient in the one or more documents. In particular, as discussed above, in some embodiments, TF-IDF analysis is performed on the one or more documents related to the medical condition of the user. In some embodiments, determining the relevance of the ingredients also includes accessing a medical profile of the user to determine the user's medical condition and correlating the medical condition to documents in one or more medical condition databases to identify the one or more documents related to the medical condition of the user.

Additionally, determining the relevance of the ingredients can include selecting a subset of the plurality of ingredients having a highest number of occurrences based on the respective first relevance rank for each of the plurality of ingredients and performing sentiment analysis of the one or more documents for the selected subset of the plurality of ingredients having the highest number of occurrences, as discussed above. The relevance of the ingredients can be updated or a second relevance rank can be done on the subset of ingredients based on the sentiment analysis, as discussed above.

At block 506, a product risk score for the product is calculated based on the updated relevance or second relevance rank of the subset of ingredients, as discussed above. For example, in some embodiments, a numerical score is computed for an average of the relevance of the ingredients of the product. In other embodiments, the computed score is one of a predetermined number of categories, as discussed above. In some embodiments, the product risk score is further based on respective quantities of the ingredients, as discussed above.

At block 508, a display on a device is modified to indicate the product risk score for the product during the same time period in which the advertisement is presented to the user, as discussed above. For example, in some embodiments, the display which presents the advertisement is modified to include a banner or notification overlaying at least a portion of the advertisement. In other embodiments, a color representing the product risk score can be displayed. In some embodiments, the advertisement is presented to the user on one device and the product risk score is displayed to the user on a second, different device. In some such embodiments, the advertisement is obtained or captured via one or more sensors located near the device presenting the advertisement to the user, as discussed above. Thus, the method enables the automatic communication of a risk score for a product during the same time period in which the product is being displayed to the user which enables various advantages as discussed above.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 6, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 6 are intended to be illustrative only and that computing nodes 10 and cloud computing environment 50 can communicate with any type of computerized device over any type of network and/or network addressable connection (e.g., using a web browser).

Referring now to FIG. 7, a set of functional abstraction layers provided by cloud computing environment 50 (FIG. 6) is shown. It should be understood in advance that the components, layers, and functions shown in FIG. 7 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and risk assessment processing 96.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although specific embodiments have been illustrated and described herein, it will be appreciated by those of ordinary skill in the art that any arrangement, which is calculated to achieve the same purpose, may be substituted for the specific embodiments shown. Therefore, it is manifestly intended that this invention be limited only by the claims and the equivalents thereof.

What is claimed is:

1. A computer-implemented method for product risk assessment, the method comprising:
    analyzing, through one or more processors, an advertisement presented to a user during a first time period to identify a plurality of ingredients in a product in the advertisement;
    analyzing, through the one or more processors, one or more documents related to a medical condition of the user to determine a respective first relevance rank for each of the plurality of ingredients based, at least in part, on a number of occurrences of each ingredient in the one or more documents;
    selecting, through the one or more processors, a subset of the plurality of ingredients having a highest number of occurrences based on the respective first relevance rank for each of the plurality of ingredients;
    performing, through the one or more processors, sentiment analysis of the one or more documents for the selected subset of the plurality of ingredients having the highest number of occurrences;
    determining, through the one or more processors, a respective second relevance rank for each of the ingredients in the selected subset of the plurality of ingredients based on the sentiment analysis;
    computing, through the one or more processors, a product risk score for the product based on the respective second relevance rank for each of the ingredients in the subset of the plurality of ingredients, the product risk score indicating a risk for effects of the product on the medical condition of the user; and
    modifying, through the one or more processors, a display on a device associated with the user such that the display:
        displays the advertisement presented to the user during the first time period; and
        indicates the product risk score for the product during the first time period in which the advertisement is presented to the user, wherein the modifying comprises overlaying a notification indicating the product risk score on top of at least a portion of the advertisement.

2. The method of claim 1, wherein the advertisement is presented to the user on a first device and wherein modifying the display on the device associated with the user comprises modifying a display on a second device different from the first device.

3. The method of claim 2, further comprising capturing, via one or more sensors, audio and images of the advertisement presented to the user on the first device, the one or more sensors located near the first device.

4. The method of claim 1, wherein analyzing the one or more documents related to the user's medical condition to determine a respective first relevance rank for each of the plurality of ingredients comprises performing term frequency-inverse document frequency analysis on the one or more documents for the plurality of ingredients.

5. The method of claim 1, further comprising determining, through one or more processors, a quantity of each of the plurality of ingredients in the product; and
    wherein computing the product risk score for the product further comprises computing the product risk score based on the determined quantity of each of the plurality of ingredients in the product.

6. The method of claim 4, wherein analyzing the advertisement presented to the user during the first time period to identify the plurality of ingredients in the product in the advertisement comprises:
    performing image analysis to identify a barcode of the product;
    identifying the product in a product database based on the identified barcode; and
    obtaining the plurality of ingredients and quantity of each of the ingredients in the product from the product database.

7. An apparatus comprising:
    a display;
    a network interface; and
    a processor communicatively coupled with the display and the network interface, the processor configured to:
        analyze an advertisement presented to a user during a first time period to identify a plurality of ingredients in a product in the advertisement;
        retrieve, from one or more databases via the network interface, one or more documents related to a medical condition of a user viewing the advertisement;
        analyze the one or more documents to determine a respective relevance of each of the plurality of ingredients to the product based, at least in part, on a respective number of occurrences of each ingredient in the one or more documents;
        select a subset of the plurality of ingredients having a highest number of occurrences in the one or more documents;
        update the respective relevance of each ingredient in the subset of plurality of ingredients based on sentiment analysis of the one or more documents for the selected subset of the plurality of ingredients having the highest number of occurrences;
        compute a product risk score for the product based on the updated respective relevance for each of the ingredients in the subset of the plurality of ingredients, the product risk score indicating a risk for effects of the product on the medical condition of the user; and
        output instructions to the display to:
            display the advertisement presented to the user during the first time period; and
            display information indicating the product risk score for the product during the first time period in which the advertisement is presented to the user, including overlay of a notification indicating the product risk score on top of at least a portion of the advertisement.

8. The apparatus of claim 7, further comprising:
one or more sensors configured to capture audio and images of the advertisement presented to the user on a separate device.

9. The apparatus of claim 7, wherein the processor is configured to perform term frequencyinverse document frequency analysis on the one or more documents for the plurality of ingredients to determine the respective relevance of each of the plurality of ingredients to the product.

10. The apparatus of claim 7, wherein the processor is further configured to:
determine a quantity of each of the plurality of ingredients in the product; and
compute the product risk score for the product based on the determined quantity of each of the plurality of ingredients in the product.

11. The apparatus of claim 10, wherein the processor is further configured to:
perform image analysis on the advertisement to identify a barcode of the product;
identify the product in a product database based on the identified barcode, the product database coupled to the processor via the network interface; and
obtain the plurality of ingredients and quantity of each of the ingredients in the product from the product database.

12. A computer program product comprising a computer readable storage medium having a computer readable program stored therein, wherein the computer readable program, when executed by a processor, causes the processor to:
analyze an advertisement presented to a user during a first time period to identify a plurality of ingredients in a product in the advertisement;
retrieve, from one or more databases, one or more documents related to a medical condition of a user viewing the advertisement;
analyze the one or more documents to determine a respective relevance of each of the plurality of ingredients to the product based, at least in part, on a respective number of occurrences of each ingredient in the one or more documents;
select a subset of the plurality of ingredients having a highest number of occurrences in the one or more documents;
update the respective relevance of each ingredient in the subset of plurality of ingredients based on sentiment analysis of the one or more documents for the selected subset of the plurality of ingredients having the highest number of occurrences;
compute a product risk score for the product based on the updated respective relevance for each of the ingredients in the subset of the plurality of ingredients, the product risk score indicating a risk for effects of the product on the medical condition of the user; and
output instructions to a display to:
display the advertisement presented to the user during the first time period; and
display information indicating the product risk score for the product during the first time period in which the advertisement is presented to the user including overlay of a notification indicating the product risk score on top of at least a portion of the advertisement.

13. The computer program product of claim 12, wherein the program instructions are further configured to cause the processor to analyze audio and images of the advertisement captured by one or more sensors located near a first device configured to present the advertisement to the user and to output instructions to a display on a second device different from the first device to display the information indicating the product risk score for the product during the first time period.

14. The computer program product of claim 12, wherein the program instructions are further configured to cause the processor to perform term frequency-inverse document frequency analysis on the one or more documents for the plurality of ingredients to determine the respective relevance of each of the plurality of ingredients to the product.

15. The computer program product of claim 12, wherein the program instructions are further configured to cause the processor to:
determine a quantity of each of the plurality of ingredients in the product; and
compute the product risk score for the product based on the determined quantity of each of the plurality of ingredients in the product.

16. The computer program product of claim 12, wherein the program instructions are further configured to cause the processor to:
perform image analysis on the advertisement to identify a barcode of the product;
identify the product in a product database based on the identified barcode; and
obtain the plurality of ingredients and quantity of each of the ingredients in the product from the product database.

* * * * *